US009867566B2

(12) United States Patent
Brickman et al.

(10) Patent No.: US 9,867,566 B2
(45) Date of Patent: Jan. 16, 2018

(54) TECHNOLOGIES FOR WHITE MATTER HYPERINTENSITY QUANTIFICATION

(71) Applicants: Adam M. Brickman, Bronx, NY (US); Jordan Muraskin, New York, NY (US); Frank A. Provenzano, New York, NY (US); Atul Narkhede, New York, NY (US)

(72) Inventors: Adam M. Brickman, Bronx, NY (US); Jordan Muraskin, New York, NY (US); Frank A. Provenzano, New York, NY (US); Atul Narkhede, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 72 days.

(21) Appl. No.: 14/947,704

(22) Filed: Nov. 20, 2015

(65) Prior Publication Data
US 2016/0143573 A1 May 26, 2016

Related U.S. Application Data

(60) Provisional application No. 62/082,697, filed on Nov. 21, 2014.

(51) Int. Cl.
*A61B 5/00* (2006.01)
*A61B 5/055* (2006.01)
(Continued)

(52) U.S. Cl.
CPC ............ *A61B 5/4064* (2013.01); *A61B 5/055* (2013.01); *A61B 5/7425* (2013.01);
(Continued)

(58) Field of Classification Search
CPC ......... G06T 7/11; G06T 7/136; G06T 7/0012; G06T 2207/20076; G06T 2207/10088;
(Continued)

(56) References Cited

U.S. PATENT DOCUMENTS 6,430,430 B1 * 8/2002 Gosche ................. G06T 7/0012
128/920

FOREIGN PATENT DOCUMENTS

WO  WO2000065985  11/2000
WO  WO2009097612  8/2009
WO  WO2013057697  4/2013

OTHER PUBLICATIONS

Samaille et al. "Automatic Segmentation of Age-Related White Matter Changes on FLAIR Images: Method and Multicentre Validation." IEEE International Symposium on Biomedical Imaging: From Nano to Macro, Mar. 30, 2011—pp. 2014-2017.*

(Continued)

*Primary Examiner* — Jon Chang
(74) *Attorney, Agent, or Firm* — Dentons US LLP

(57) ABSTRACT

A method comprises selecting, via a computer, an intensity threshold value. The method also comprises defining, via the computer, a plurality of hyperintensities on imaging data based on the intensity threshold value. The method further comprises extracting, via the computer, a plurality of voxels from the imaging data based on the defining. The method additionally comprises determining, via the computer, a total volume of the voxels based on the extracting. The method also comprises determining, via the computer, a regional distribution of WMH based on an anatomical atlas and the total volume.

24 Claims, 9 Drawing Sheets

(51) Int. Cl.
*G06K 9/46* (2006.01)
*G06T 15/08* (2011.01)
*G06T 7/00* (2017.01)
*G06T 7/11* (2017.01)
*G06T 7/136* (2017.01)
*A61B 5/16* (2006.01)

(52) U.S. Cl.
CPC .......... *G06K 9/4604* (2013.01); *G06T 7/0012* (2013.01); *G06T 7/11* (2017.01); *G06T 7/136* (2017.01); *A61B 5/16* (2013.01); *A61B 2576/026* (2013.01); *G06T 2207/10088* (2013.01); *G06T 2207/20076* (2013.01); *G06T 2207/30016* (2013.01)

(58) Field of Classification Search
CPC ........ G06T 2207/30016; A61B 5/4064; A61B 5/055; A61B 5/7425; A61B 5/16; A61B 2576/026; G06K 9/4604
See application file for complete search history.

(56) References Cited

OTHER PUBLICATIONS

Raniga et al. "Local Intensity Model: An Outlier Detection Framework with Applications to White Matter Hyperintensity Segmentation." IEEE International Symposium on Biomedical Imaging: From Nano to Macro, Mar. 30, 2011—pp. 2057-2060.*

Iheme et al. "Concordance Between Computer-based Neuroimaging Findings and Expert Assessments in Dementia Grading." 21st Signal Processing and Communications Applications Conference, Apr. 24, 2013, 4 pages.*

Admiraal-Behloul et al., Fully automatic segmentation of white matter hyperintensities in MR images of the elderly, NeuroImage, 2005, vol. 28, Issue 3, pp. 607-617.

Brickman et al., Quantitative approaches for assessment of white matter hyperintensities in elderly populations, Psychiatry Research: Neuroimaging, 2011, vol. 193, pp. 101-106.

Brickman et al., Regional white matter hyperintensity volume, not hippocampal atrophy, predicts incident Alzheimer's disease in a community-based cohort,Archives of Neurology, 2012, vol. 69, pp. 1621-1627.

Brikman et al., Structural neuroimaging in Alzheimer's disease: Do white matter hyperintensities matter? Dialogues in Clinical neuroscience, 2009, vol. 11, pp. 81-190.

Maillard et al., An automated procedure for the assessment of white matter hyperintensities by multispectral (T1, T2, PD) MRI and an evaluation of its between-centre reproducibility based on two large community databases, Neuroradiology, 2008, vol. 50, pp. 31-42.

Meier et al., White matter predictors of cognitive functioning in older adults, Journal of the International Neuropsychological Society, 2012, vol. 18, pp. 414-427.

Sachdev et al., Reliability and validity of ratings of signal hyperintensities on MRI by visual inspection and computerized measurement, Psychiatry Res, 1999, vol. 92, pp. 103-115.

Brickman et al., Enhancing dentate gyrus function with dietary flavanols improves cognition in older adults, Nature Neuroscience, 2014, vol. 17, pp. 1798-1803.

* cited by examiner

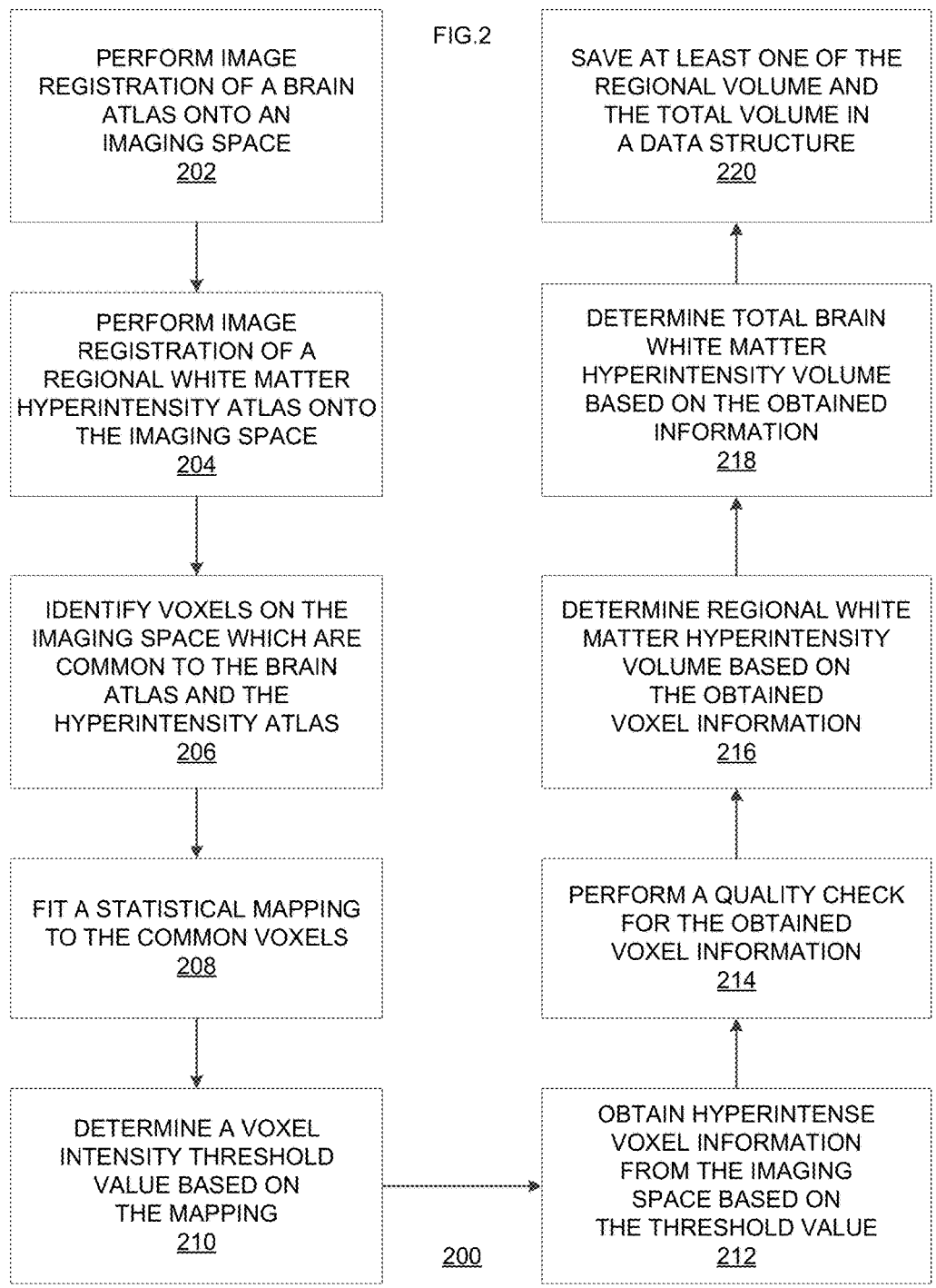

TECHNOLOGIES FOR WHITE MATTER HYPERINTENSITY QUANTIFICATION

CROSS REFERENCE TO RELATED APPLICATIONS

The present application claims the benefit of U.S. Provisional Application Ser. No. 62/082,697 filed 21 Nov. 2014, which is incorporated herein by reference in its entirety.

STATEMENT REGARDING FEDERALLY SPONSORED RESEARCH OR DEVELOPMENT

This invention was made with government support under Grants R01 AG034189 and K23 AG029949 awarded by The National Institutes of Health. The government has certain rights in the invention.

TECHNICAL FIELD

Generally, the present disclosure relates to computing. More particularly, the present disclosure relates to imaging.

BACKGROUND

In the present disclosure, where a document, an act and/or an item of knowledge is referred to and/or discussed, then such reference and/or discussion is not an admission that the document, the act and/or the item of knowledge and/or any combination thereof was at the priority date, publicly available, known to the public, part of common general knowledge and/or otherwise constitutes prior art under the applicable statutory provisions; and/or is known to be relevant to an attempt to solve any problem with which the present disclosure is concerned with. Further, nothing is disclaimed.

Magnetic resonance imaging (MRI) is a technology which has many uses. One of such uses is human brain imaging for medical purposes or research purposes. During such brain imaging, white matter hyperintensities (WMH) are often detected within a cerebral white matter portion of the human brain. Presence of WMH can symptomatically correlate to cognitive disorders, neurological disorders, or psychiatric disorders, such as depression or dementia. Resultantly, in order to obtain more precise information, patient evaluations are desired. However, such evaluations frequently rely on patient interviews, which can be imprecise or biased. Accordingly, there is a need for a technology to address such drawbacks.

BRIEF SUMMARY

The present disclosure at least partially address at least one of the above. However, the present disclosure can prove useful to other technical areas. Therefore, the claims should not be construed as necessarily limited to addressing any of the above.

An example embodiment of the present disclosure includes a method which comprises selecting, via a computer, an intensity threshold value. The method also comprises defining, via the computer, a plurality of hyperintensities on imaging data based on the intensity threshold value. The method further comprises extracting, via the computer, a plurality of voxels from the imaging data based on the defining. The method additionally comprises determining, via the computer, a total volume of the voxels based on the extracting. The method also comprises determining, via the computer, a regional distribution of WMH based on an anatomical atlas and the total volume.

In some embodiments of the method, the intensity threshold value is selected from a range of specificity-to-sensitivity intensity threshold values.

In some embodiments of the method, the selecting is based on image analysis based on at least one of image brightness information, image historic information, image degradation information, and imaging machine information.

In some embodiments, the method further comprises analyzing, via the computer, the imaging data for at least one of hyperintensity under-labeling and hyperintensity over-labeling based on at least one of voxel location and voxel light intensity.

In some embodiments, the method further comprises editing, via the computer, the imaging data based on the analyzing.

An example embodiment of the present disclosure includes a system which comprises a hardware processor and a memory operably coupled to the hardware processor. The memory stores a set of instructions for execution via the hardware processor. The instructions instruct the hardware processor to perform a method comprising: selecting an intensity threshold value; defining a plurality of hyperintensities on imaging data based on the intensity threshold value; extracting a plurality of voxels from the imaging data based on the defining; determining a total volume of the voxels based on the extracting; and determining a regional distribution of WMH based on an anatomical atlas and the total volume.

In some embodiments of the system, in the method, the intensity threshold value is selected from a range of specificity-to-sensitivity intensity threshold values.

In some embodiments of the system, in the method, the selecting is based on image analysis based on at least one of image brightness information, image historic information, image degradation information, and imaging machine information.

In some embodiments of the system, the method further comprises analyzing the imaging data for at least one of hyperintensity under-labeling and hyperintensity over-labeling based on at least one of voxel location and voxel light intensity.

In some embodiments of the system, the method further comprises editing, via the computer, the imaging data based on the analyzing.

An example embodiment of the present disclosure includes a non-transitory computer-readable storage medium storing a set of instructions for execution via a processing circuit to implement a method comprising: selecting, via a computer, an intensity threshold value; defining, via the computer, a plurality of hyperintensities on imaging data based on the intensity threshold value; extracting, via the computer, a plurality of voxels from the imaging data based on the defining; determining, via the computer, a total volume of the voxels based on the extracting; and determining, via the computer, a regional distribution of WMH based on an anatomical atlas and the total volume.

In some embodiments of the non-transitory computer-readable storage medium, the intensity threshold value is selected from a range of specificity-to-sensitivity intensity threshold values.

In some embodiments of the non-transitory computer-readable storage medium, the selecting is based on image analysis based on at least one of image brightness information, image historic information, image degradation information, and imaging machine information.

In some embodiments of the non-transitory computer-readable storage medium, the method further comprising: analyzing, via the computer, the imaging data for at least one of hyperintensity under-labeling and hyperintensity over-labeling based on at least one of voxel location and voxel light intensity.

In some embodiments of the non-transitory computer-readable storage medium, the method further comprising: editing, via the computer, the imaging data based on the analyzing.

BRIEF DESCRIPTION OF THE DRAWINGS

The accompanying drawings illustrate example embodiments of the present disclosure. Such drawings are not to be construed as necessarily limiting the disclosure. Like numbers and/or similar numbering scheme can refer to like and/or similar elements throughout.

FIG. 2 shows a flowchart of an example embodiment of a process for a WMH quantification according to the present disclosure.

DETAILED DESCRIPTION OF THE PREFERRED EMBODIMENTS

Figure 1A:
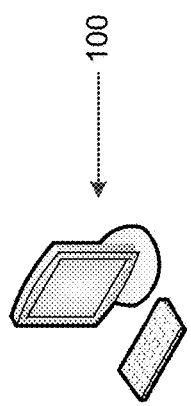
FIG. 1A shows a perspective view of an example embodiment of a desktop computer according to the present disclosure.

The present disclosure is now described more fully with reference to the accompanying drawings, in which example embodiments of the present disclosure are shown. The present disclosure can, however, be embodied in many different forms and should not be construed as necessarily being limited to the example embodiments disclosed herein. Rather, these example embodiments are provided so that the present disclosure is thorough and complete, and fully conveys the concepts of the present disclosure to those skilled in the relevant art. In addition, features described with respect to certain example embodiments can be combined in and/or with various other example embodiments. Different aspects and/or elements of example embodiments, as disclosed herein, can be combined in a similar manner.

The terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from the teachings of the present disclosure.

The terminology used herein is for describing particular example embodiments and is not intended to be necessarily limiting of the present disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence and/or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" can be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings were turned over, then the elements described as being on the "lower" side of other elements would then be oriented on "upper" sides of the other elements. Similarly, if the device in one of the figures were turned over, elements described as "below" or "beneath" other elements would then be oriented "above" the other elements. Therefore, the example terms "below" and "lower" can encompass both an orientation of above and below.

As used herein, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

As used herein, the term "about" and/or "substantially" refers to a +/−10% variation from the nominal value/term. Such variation is always included in any given value/term provided herein, whether or not such variation is specifically referred thereto.

If any disclosures are incorporated herein by reference and such disclosures conflict in part and/or in whole with the present disclosure, then to the extent of conflict, and/or broader disclosure, and/or broader definition of terms, the present disclosure controls. If such disclosures conflict in part and/or in whole with one another, then to the extent of conflict, the later-dated disclosure controls.

FIG. 1A shows a perspective view of an example embodiment of a desktop computer according to the present disclosure. A desktop computer 100 is used for WMH quantification, as described herein. However, note that other types of computers or computer systems can also be configured for WMH quantification, as described herein. For example, such computer can be a workstation computer, a laptop computer, a terminal computer, a tablet computer, a mobile phone, an eyewear computer, a server computer, a medical imaging machine, a cloud-computing system, a mainframe, a supercomputer, or other suitable computers.

Figure 1B:
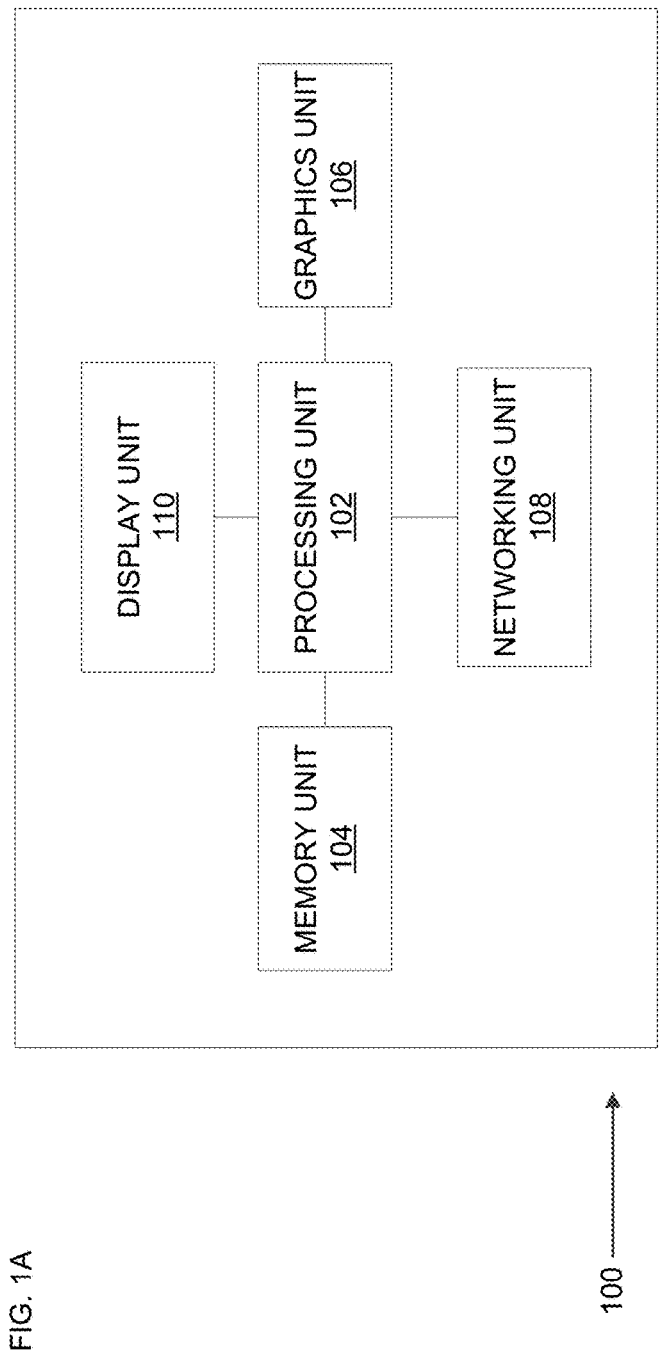
FIG. 1B shows a schematic view of an example embodiment of the desktop computer according to the present disclosure.

FIG. 1B shows a schematic view of an example embodiment of a computer according to the present disclosure. The computer 100 comprises a processing unit 102, a memory unit 104 operably coupled to the processing unit 102, a graphics unit 106 operably coupled to the processing unit 102, a networking unit 108 operably coupled to the processing unit 102, and a display unit 110 operably coupled to the processing unit 102. The computer 100 is powered via mains electricity, such as via a power cable. In other embodiments, the computer 100 is powered via at least one of an onboard rechargeable battery, such as a lithium-ion battery, and an onboard renewable energy source, such as a photovoltaic cell or a hydropower turbine. Note that the computer 100 can be operably coupled to at least one user input device, such as a computer keyboard, a computer mouse, a touchpad, a touchscreen, or other suitable user input devices. Note that each of components of the computer 100 can be at least partially implemented in logic, whether hardware-based or software-based. For example, when the logic is hardware-based, then such logic can comprise circuitry, such as processors, memory, input devices, output devices, or other hardware, that is configured, such as via programming or design, to implement a functionality of a respective component. Likewise, when the logic is software-based, then such logic can comprise one or more instructions, such as assembly code, machine code, object code, source code, or any other type of instructions, which when executed, such as via running or compilation, implement a functionality of a respective component. Further, note that at least one of such components can be implemented as a service. Moreover, note that at least two of such components can be hosted on one computing system/hardware/device or each be distinctly hosted.

The processing unit 102 comprises a hardware processor, such as a multicore processor. For example, the processing unit 102 comprises a central processing unit (CPU).

The memory unit 104 comprises a computer-readable storage medium, which can be non-transitory. The medium stores a plurality of computer-readable instructions for execution via the processing unit 102. The instructions instruct the processing unit 102 to facilitate performance of a method for WMH quantification, as described herein. Some examples of the memory unit 104 comprise a volatile memory unit, such as random access memory (RAM) unit, or a non-volatile memory unit, such as an electrically addressed memory unit or a mechanically addressed memory unit. For example, the electrically addressed memory comprises a flash memory unit. For example, the mechanically addressed memory unit comprises a hard disk drive. The memory unit 104 is in wired communication with the processing unit 102.

The memory unit 104 can include, be a part of, or is a storage medium, such as at least one of a data repository, a data mart, or a data store. For example, the storage medium is a database, such as a relational database, a non-relational database, an in-memory database, or others, which can store data and allow access to such data to a storage controller, whether directly and/or indirectly, whether in a raw state, a formatted state, an organized stated, or any other accessible state. The memory unit 104 can include, be a part of, or is any type of storage, such as primary storage, secondary storage, tertiary storage, off-line storage, volatile storage, non-volatile storage, semiconductor storage, magnetic storage, optical storage, flash storage, hard disk drive storage, floppy disk drive, magnetic tape, or other data storage medium. The memory unit 104 is configured for various file or data I/O operations, including reading, writing, editing, deleting, updating, searching, selecting, merging, or others.

The graphics unit 106 comprises a graphics processing unit (GPU) for image processing. The graphics unit 106 is a graphics dedicated unit, but in other embodiments, the processing unit 102 is integrated with the graphics unit 106. For example, the graphics unit 106 comprises a video card. The graphics unit 106 is in wired communication with the processing unit 102.

The networking unit 108 comprises a network interface controller for computer network communication, whether wired or wireless. For example, the networking unit 108 comprises a hardware unit for computer networking communication based on at least one standard selected from a set of Institute of Electrical and Electronics Engineers (IEEE) 802 standards, such as an IEEE 802.11 standard. For instance, the networking unit 108 comprises a wireless network card operative according to a IEEE 802.11(g) standard. The networking unit 108 is in wired communication with the processing unit 102.

The networking unit 108 can be operate in accordance with a network topology based on a distributed network operation model which allocates tasks/workloads between servers, which provide a resource/service, and clients, which request the resource/service. The servers and the clients illustrate different computers/applications, but in some embodiments, the servers and the clients reside in or are one system/application. Further, in some embodiments, the network topology can entails allocating a large number of resources to a small number of computers, such as the servers, where complexity of the clients depends on how much computation is offloaded to the number of computers, i.e., more computation offloaded from the clients onto the servers leads to lighter clients, such as being more reliant on network sources and less reliant on local computing resources. Note that other computing models are possible as well. For example, such models can comprise decentralized computing, such as peer-to-peer (P2P), for instance Bit-Torrent®, or distributed computing, such as via a computer cluster where a set of networked computers works together such that the computer can be viewed as a single system.

The network can include a plurality of nodes, such as a collection of computers and/or other hardware interconnected via a plurality of communication channels, which allow for sharing of resources and/or information. Such interconnection can be direct and/or indirect. The network can be wired and/or wireless. The network can allow for communication over short and/or long distances, whether encrypted and/or unencrypted. The network can operate via at least one network protocol, such as Ethernet, a Transmission Control Protocol (TCP)/Internet Protocol (IP), and so forth. The network can have any scale, such as a personal area network, a local area network, a home area network, a storage area network, a campus area network, a backbone network, a metropolitan area network, a wide area network, an enterprise private network, a virtual private network, a virtual network, a satellite network, a computer cloud network, an internetwork, a cellular network, and so forth. The network can be and/or include an intranet and/or an extranet. The network can be and/or include Internet. The network can include other networks and/or allow for communication with other networks, whether sub-networks and/or distinct networks, whether identical and/or different from the network in structure or operation. The network can include hardware, such as a computer, a network interface card, a repeater, a hub, a bridge, a switch, an extender, an antenna, and/or a firewall, whether hardware based and/or software based. The network can be operated, directly and/or indirectly, by and/or on behalf of one and/or more entities or actors, irrespective of any relation to contents of the present disclosure.

When the networking unit 108 operates on a client/server architecture, then the server can be hardware-based and/or software-based. The server is and/or can be hosted on, whether directly and/or indirectly, a server computer, whether stationary or mobile, such as a kiosk, a workstation, a vehicle, whether land, marine, or aerial, a desktop, a laptop, a tablet, a mobile phone, a mainframe, a supercomputer, a server farm, and so forth. The server computer can include and/or be a part of another computer system and/or a cloud computing network. The server computer can run any type of operating system (OS), such as MacOS®, Windows®, Android®, Unix®, Linux® and/or others. The server computer can include and/or be coupled to, whether directly and/or indirectly, an input device, such as a mouse, a keyboard, a camera, whether forward-facing and/or back-facing, an accelerometer, a touchscreen, a biometric reader, a clicker, and/or a microphone. The server computer can include and/or be coupled to, whether directly and/or indirectly, an output device, such as a display, a speaker, a headphone, a joystick, a videogame controller, a vibrator, and/or a printer. In some embodiments, the input device and the output device can be embodied in one unit, such as a touch-enabled display, which can be haptic. The server computer can include circuitry for geolocation/global positioning determination, such as via a global positioning system (GPS), a signal triangulation system, and so forth. The server computer can be equipped with near-field-communication (NFC) circuitry. The server computer can host, run, and/or be coupled to, whether directly and/or indirectly, a database, such as a relational database or a non-relational database, such as a post-relational database, an in-memory database, or others, which can feed, avail, or otherwise provide data to the server, whether directly and/or indirectly. The server computer, can be in communication with the network, such as directly and/or indirectly, selectively and/or unselectively, encrypted and/or unencrypted, wired and/or wireless. Such communication can be via a software application, a software module, a mobile app, a browser, a browser extension, an OS, and/or any combination thereof. For example, such communication can be via a common framework/application programming interface (API), such as Hypertext Transfer Protocol Secure (HTTPS). More that one server can be used.

Likewise, the client can be hardware-based and/or software-based. The client can be and/or is hosted on, whether directly and/or indirectly, a client computer, whether stationary or mobile, such as a terminal, a kiosk, a workstation, a vehicle, whether land, marine, or aerial, a desktop, a laptop, a tablet, a mobile phone, a mainframe, a supercomputer, a server farm, and so forth. The client computer can include and/or be a part of another computer system and/or cloud computing network. The client computer can run any type of OS, such as MacOS®, Windows®, Android®, Unix®, Linux® and/or others. The client computer can include and/or be coupled to an input device, such as a mouse, a keyboard, a camera, whether forward-facing and/or back-facing, an accelerometer, a touchscreen, a biometric reader, a clicker, and/or a microphone, and/or an output device, such as a display, a speaker, a headphone, a joystick, a videogame controller, a vibrator, and/or a printer. In some embodiments, the input device and the output device can be embodied in one unit, such as a touch-enabled display, which can be haptic. The client computer can include circuitry for geolocation/global positioning determination, such as via a GPS, a signal triangulation system, and so forth. The client computer can be equipped with NFC circuitry. The client computer can host, run and/or be coupled to, whether directly and/or indirectly, a database, such as a relational database or a non-relational database, such as a post-relational database, an in-memory database, or others, which can feed or otherwise provide data to the client, whether directly and/or indirectly. More than one client can be used. The client, via the client computer, is in communication with the network, such as directly and/or indirectly, selectively and/or unselectively, encrypted and/or unencrypted, wired and/or wireless, via contact and/or contactless. Such communication can be via a software application, a software module, a mobile app, a browser, a browser extension, an OS, and/or any combination thereof. For example, such communication can be via a common framework/API, such as HTTPS. In some embodiments, the server and the client can also directly communicate with each other, such as when hosted in one system or when in local proximity to each other, such as via a short range wireless communication protocol, such as infrared or Bluetooth®. Such direct communication can be selective and/or unselective, encrypted and/or unencrypted, wired and/or wireless, via contact and/or contactless. Since many of the clients can initiate sessions with the server relatively simultaneously, in some embodiments, the server employs load-balancing technologies and/or failover technologies for operational efficiency, continuity, and/or redundancy.

The display unit 110 comprises a display for displaying information. The display comprises at least one of an electronic visual display, a flat panel display, a liquid crystal display (LCD), an electrophoretic display, and a volumetric display. For example, the display unit 110 comprises a touch-enabled computer monitor. The display unit 110 is in wired communication with the processing unit 102.

In one mode of operation, the computer 100 runs such that a method for WMH quantification, as described herein, is performed, such as based on receiving a user request input via the display unit 110. The computer 100 displays a result of the method via the display unit 110 based on operation of the graphics unit 106. Optionally, the computer 100 communicates the result to another computer over a computer network via the networking unit 108, such as based on receiving a user request input via the display unit 110.

In another mode of operation, the computer 100 runs such that a method for WMH quantification, as described herein, is performed, such as based on receiving a remotely input user request. The computer 100 communicates the result to a user computer over a computer network via the networking unit 108, such as based on receiving a remotely input user request. Such mode of operation can be based on a cloud computing model.

FIG. 2 shows a flowchart of an example embodiment of a process for a WMH quantification according to the present disclosure. A process 200 is used for WMH quantification. The process 200 is performed via at least one actor, such as via a user operating the computer 100 for various file and network operations, as disclosed herein. The process 200 includes a plurality of blocks 202-210, which are performed consecutively. However, in other embodiments, non-consecutive performance is possible, such as block 218 preceding block 216.

In block 202, the computer 100 performs image registration of a brain atlas onto an imaging space. The performance is automated, such as based on receiving a user request. The image registration is non-linear, but other types of image registration are possible, such as a label based approach, an intensity based approach, or a hybrid/combination thereof. The brain atlas is a referential brain structure mapping, which can be a standardized brain atlas. For example, the brain atlas is a Montreal Neurological Institute (MNI) brain atlas. The imaging space is a fluid attenuated inversion recovery (FLAIR) imaging space, but other types of imaging spaces are possible. Such image registration is performed via a non-linear warp/spatial transformation and a transformation matrix, both of which are saved for subsequent use. Note that, in some embodiments, at least one of an intensity normalization, an image reorientation, and a brain extraction can occur before, during, or after performance of block 202.

In block 204, the computer 100 performs image registration of a regional WMH atlas onto the imaging space. The performance is automated, such as based on receiving a user request. The image registration is non-linear, but other types of image registration are possible, such as a label based approach, an intensity based approach, or a hybrid/combination thereof. The image registration is performed via the non-linear warp/spatial transformation and the transformation matrix, both of which come from block 202.

The regional WMH atlas illustrates a distribution of WMH location probability. The regional WMH atlas is data-sourced via the computer 100 from a plurality of imaging datasets. The datasets are obtained via medical imaging, such as via MRI scanning. For example, the datasets can be FLAIR based. However, in some embodiments, the WMH atlas is non-regionally separated and for example comprises a WMH location probability.

The medical imaging is of a plurality of human subjects which participated in a study. Each of the datasets corresponds to each of the subjects. The subjects are randomly selected from the study for the medical imaging. For example, the study is a community-based epidemiological study of older adults, such as over 65 years of age. One example of such study is a Washington Heights/Hamilton Heights Aging Project (WHICAP).

More particularly, the regional WMH atlas is created, such as via the computer 100, from a plurality of datasets corresponding to a plurality of human subjects which participated in a study of cognitive aging and dementia. For example, 253 datasets uniquely correspond to 253 human subjects. However, other number of datasets, whether greater or lesser than 253 can also be used. The regional WMH atlas comprises of a plurality of voxels that have a high probability, such as about 52%, of being hyperintense among older adults.

The regional WMH atlas is created, such as via the computer 100, via a plurality of steps. For example, first, the computer 100 registers a unique final WMH map to the MNI atlas, such as MNI152_T1_2 mm atlas provided in Functional Magnetic Resonance Imaging of the Brain Standard Library (FSL) standard atlases. The computer 100 obtains the final WMH map from running WMH extraction algorithm on the 253 datasets, which are FLAIR based. Second, the computer 100 sums the final WMH maps and then the computer 100 divides each voxel value by a total number of the datasets, i.e., 253, which correspond to a number of the human subjects. Such calculation provides an average voxel intensity. Third, the computer 100 applies a 1% threshold smoothing filter to the average voxel intensity, as obtained in a previous step, and converts the filtered map into a binary image representative of probable WMH representation. Such application enables a creation of an approximation which captures important data patterns, such as the distribution of the WMH location probability, while leaving out noise. Fourth, the computer 100 adds a unique identifier to the regions of interest in the probable WMH representation. More particularly, the computer 100 labels voxels specific to each region of interest with a unique intensity value. For example, a region of interest includes at least one of a frontal lobe, a parietal lobe, an occipital lobe, a temporal lobe, a cerebellum segment, a basal ganglia segment, and an insula segment. The hyperintense voxels from the probable WMH representation, which were not included in the above regions of interest, are assigned a separate identifier via the computer 100. Accordingly, the resulting atlas is the regional WMH atlas. When the regional WMH atlas is image registered onto the imaging space, then the regional WMH atlas, as image registered on the imaging space, is saved via the computer 100 for subsequent use, such as at least via the computer 100.

Note that in some embodiments, initially, in order to create the regional WMH atlas, the computer 100 runs an algorithm, as described above, but since the regional WMH atlas is not yet in existence to limit a searching space, an entire brain image is used. For example, after the image registration of the regional WMH atlas onto the image space, brain extraction function in FSL is performed on a subject's FLAIR dataset. Such action provides voxels which are in the brain, but do not include skull, dura mater, eye sockets, neck, and so forth. Such voxels are used subsequently for curve plotting, such as a Gaussian curve. However, since there is no regional segmentation performed, the computer 100 registers the regional WMH atlas, such as a lobar atlas, to each FLAIR dataset and use that registration to separate WMH by regions.

Further, note that, in some embodiments, in image analysis, a smoothing filter is used to filter out noise. Therefore, the regional WMH atlas, which is a 3D image, is a probability map, which provides a probability of WMH per voxel. For example, since a probability of 1% for a data size of 253 subjects is too low to consider, i.e., for that voxel there is a 1 in 253 chances of being hyperintense, the computer 100 deletes or ignores such voxels from the regional WMH atlas.

Additionally, note that, in some embodiments, the computer 100 converts the filtered map into the binary image to extract the voxels from subject space that have some probability of being hyperintense. Consequently, the region of the brain that the subject space is a part of is not as important until a determination if a voxel is hyperintense or not. The computer 100 converts the image into the binary image via a logical function, where if a voxel has a value more than 0, that is if a voxel has some probability more than 0 of being hyperintense, then the computer 100 labels that voxel as 1 such that the corresponding voxel in the FLAIR dataset image is considered for analysis, i.e., a data point in Gaussian curve, or else rejected.

Furthermore, note that, in some embodiments, after the computer 100 has labeled voxels as hyperintense or as normal appearing white matter, the computer 100 separates the labeled voxels based on regions. Each region of interest, such as a brain lobe, has a unique identifier to distinguish them from one another. Such identifier is used as an intensity value, where a unique intensity value is assigned to each region of interest and different intensity values appear as different colors on the regional WMH atlas for aiding in distinguishing WMH by regions.

In block 206, the computer 100 identifies voxels on the imaging space which are common to the brain atlas and the regional WMH atlas. Such identification is automated, such as based on receiving a user request. The commonality is identified via the computer 100 comparing the imaging space with the brain atlas registered thereon, as per the block 202, and the imaging space with the regional WMH atlas registered thereon, as per the block 204. Moreover, note that, in some embodiments, boundary voxels can be eroded before, during, or after, performance of block 206.

In block 208, the computer 100 fits a statistical mapping to the common voxels, as described above. Such fitting is automated, such as based on receiving a user request. The statistical mapping is a Gaussian curve, also known as a normal distribution, on a Cartesian plane having an X-axis and a Y-axis. The X-axis corresponds to a voxel intensity, which is a value corresponding to a voxel opaqueness from the imaging space with the brain atlas registered thereon. The Y-axis corresponds to a WMH frequency, which is a value corresponding to a probability from the imaging space with the regional WMH atlas image registered thereon. The common voxels are mapped onto the statistical mapping as a distribution of a voxel intensity against a WMH frequency, which can be indicative of WMH clustering. Resultantly, what is common to the imaging space with the brain atlas image registered thereon and the imaging space with the regional WMH atlas registered thereon is mapped onto the statistical mapping.

In block 210, the computer 100 determines a voxel intensity threshold value based on the mapping. Such determination is automated, such as based on receiving a user request. The threshold value functions as an optimization parameter, where the threshold value defines a lower limit of voxel intensity which should be included as a WMH. The threshold value is based on a standard deviation from a mean value. Therefore, the computer 100 defines a subject specific intensity limit as opposed to an absolute value. Such definition accommodates for variation in intensity distribution, whether in voxel contrast, voxel brightness, or both, from imaging scans from different imaging machines and different human subjects.

In some embodiments, the computer 100 selects the threshold value based on choosing randomly a plurality of datasets from the datasets uniquely corresponding to the human subjects of the study. For example, the computer 100 can be configured to select randomly between 5 to 10 datasets from the 253 datasets uniquely corresponding to 253 human subjects. However, note that the computer 100 can also be configured to select randomly less than 5 or more than 10 datasets from the datasets uniquely corresponding to the human subjects. The computer 100 then extracts WMH data from the FLAIR datasets of the randomly chosen datasets based on a plurality of different threshold values. The computer 100 selects the threshold value from the different threshold values based on a user's impression of sensitivity/specificity optimization, as observed and input into the computer 100. Note that the computer 100 can display, such as via the display unit 110, a graphical user interface (GUI) containing a scale bar, a slider, a knob, a gradual level selector, a button, or other GUI element, which enables the user to adjust the threshold value for tailoring the user's analysis to a single subject. The random selection is based on a random function executed via the computer 100.

In some embodiments, the computer 100 extracts WMH data from the FLAIR datasets of the randomly chosen datasets based on a plurality of different threshold values of at least one standard deviation from a mean, such as being higher than 3 Sigma. In order to reduce user involvement and increase automation, the computer 100 chooses a threshold value which gives the optimal specificity and sensitivity balance in a set of resulting WMH masks, as identified via the computer 100 via computer vision/heuristics based on a plurality of preset conditions, which can be updated dynamically, where at least one of the resulting WMH masks is nor over nor under labeled. For example, the computer 100 can be configured to account for a predetermined range of image specificity to image sensitivity threshold values and at least one of an image brightness information factor, a voxel location, a historical information of other images factor, an image degradation information factor, and an imaging machine information factor, such as based on a lookup table. The random selection is based on a random function executed via the computer 100.

With respect to identification of WMH volumes, the computer 100 extracts the voxels from the subjects FLAIR scans, common to regional WMH atlas, and the computer 100 applies a curve fitting algorithm to the intensity values of these voxels. The computer 100 uses a normal distribution function as the curve is to be fitted. Based on a central limit theorem, which states that a sum of independent samples from any distribution with a finite mean and variance converges to the normal distribution as sample size goes to infinity, a normal or Gaussian distribution, also known as a bell curve is a defined by formula I below:

$$y = f(x \mid \mu, \sigma) = \frac{1}{\sigma\sqrt{2\pi}} e^{\frac{-(x-\mu)^2}{2\sigma^2}}$$

Figure 9:
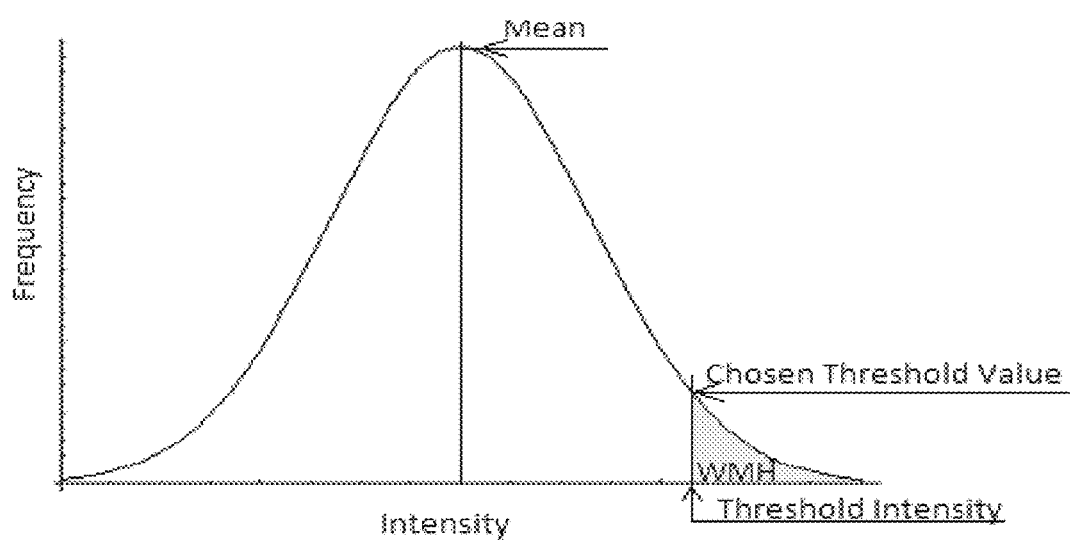
FIG. 9 shows a Gaussian curve fitting.

Accordingly, the Gaussian curve fitting provides a mean value and a standard deviation value. Such values are used as a reference to calculate the threshold intensity value, where the threshold Intensity is defined by mean+chosen Threshold Value*Standard Deviation (since WMH are higher than the mean intensity value). Therefore, all voxels with an intensity equal to or higher than the threshold intensity are labeled as WMH voxels. Subsequently, the computer 100 uses the regional WMH atlas to map out the regional distribution of such hyperintense voxels. The Gaussian curve fitting is shown in FIG. 9.
Formula I In block 212, the computer 100 obtains the hyperintense voxel information from the image space based on the threshold value. Such obtaining is automated, such as based on receiving a user request. The obtaining comprises selecting the hyperintense voxels, which exceed the threshold value, from the imaging space, as per blocks 202-206, for relevant data processing, such as volume determinations, as described herein. The obtained voxel information is saved for subsequent use, such as for quality auditing, whether manual or automatic.

In block 214, the computer 100 performs a quality check for the obtained voxel information. For example, the computer 100 checks for the threshold value which gives the optimal specificity and sensitivity balance in the set of resulting WMH masks, as identified via the computer 100 via computer vision/heuristics based on a plurality of preset conditions, which can be updated dynamically, where at least one of the resulting WMH masks is nor over nor under labeled. For example, the computer 100 can be configured to quality check based on at least one of an image brightness information factor, an image contrast information factor, a voxel location, a historical information of other images factor, an image degradation information factor, and an imaging machine information factor, such as based on a lookup table. Note that other factors can be used as well. Further, note that the quality check can comprise checking whether at least one of blocks 202-212 is properly performed. In other embodiments, block 214 is omitted.

In block 216, the computer 100 determines a regional WMH volume based on the obtained information, such as from block 212 or block 214. Such determination is automated, such as based on receiving a user request. The regional volume is based on the regional WMH atlas.

In block 218, the computer 100 determines a total brain WMH volume based on the obtained information, such as from block 212 or block 214. Such determination is automated, such as based on receiving a user request. The regional volume is based on the brain atlas and a sum of voxel cluster volumes, as obtained based on the block 206.

In block 220, the computer 100 save at least one of the regional WMH volume and the brain WMH volume in a data structure. Such saving is automated, such as based on receiving a user request. The data structure comprises at least one of a table, an array, a list, and a spreadsheet, or combinations thereof.

Figure 3:
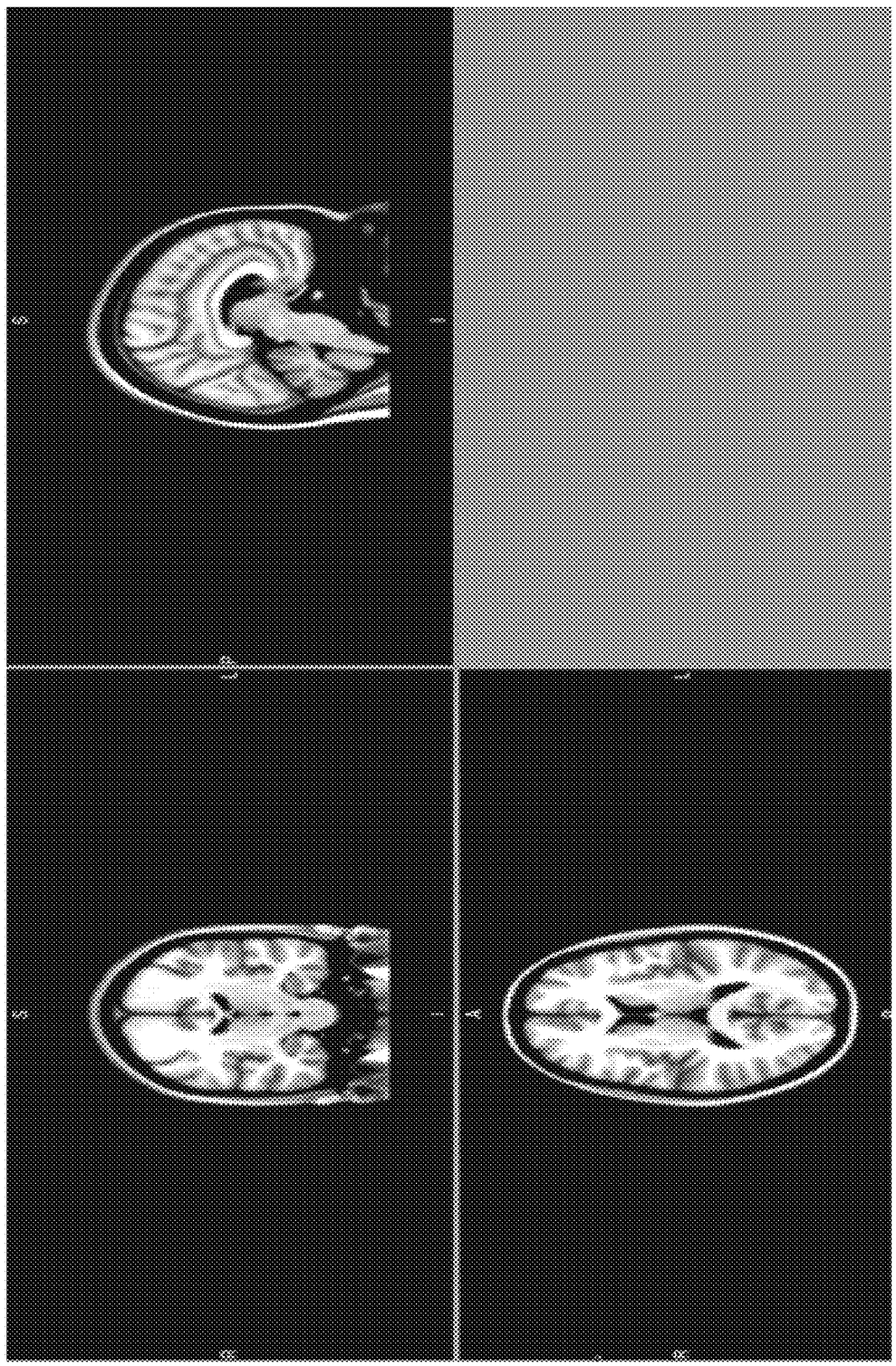
FIG. 3 shows a screenshot of an example embodiment of a brain atlas according to the present disclosure.

FIG. 3 shows a screenshot of an example embodiment of a brain atlas according to the present disclosure. As shown, the brain atlas is the MNI atlas.

Figure 4:
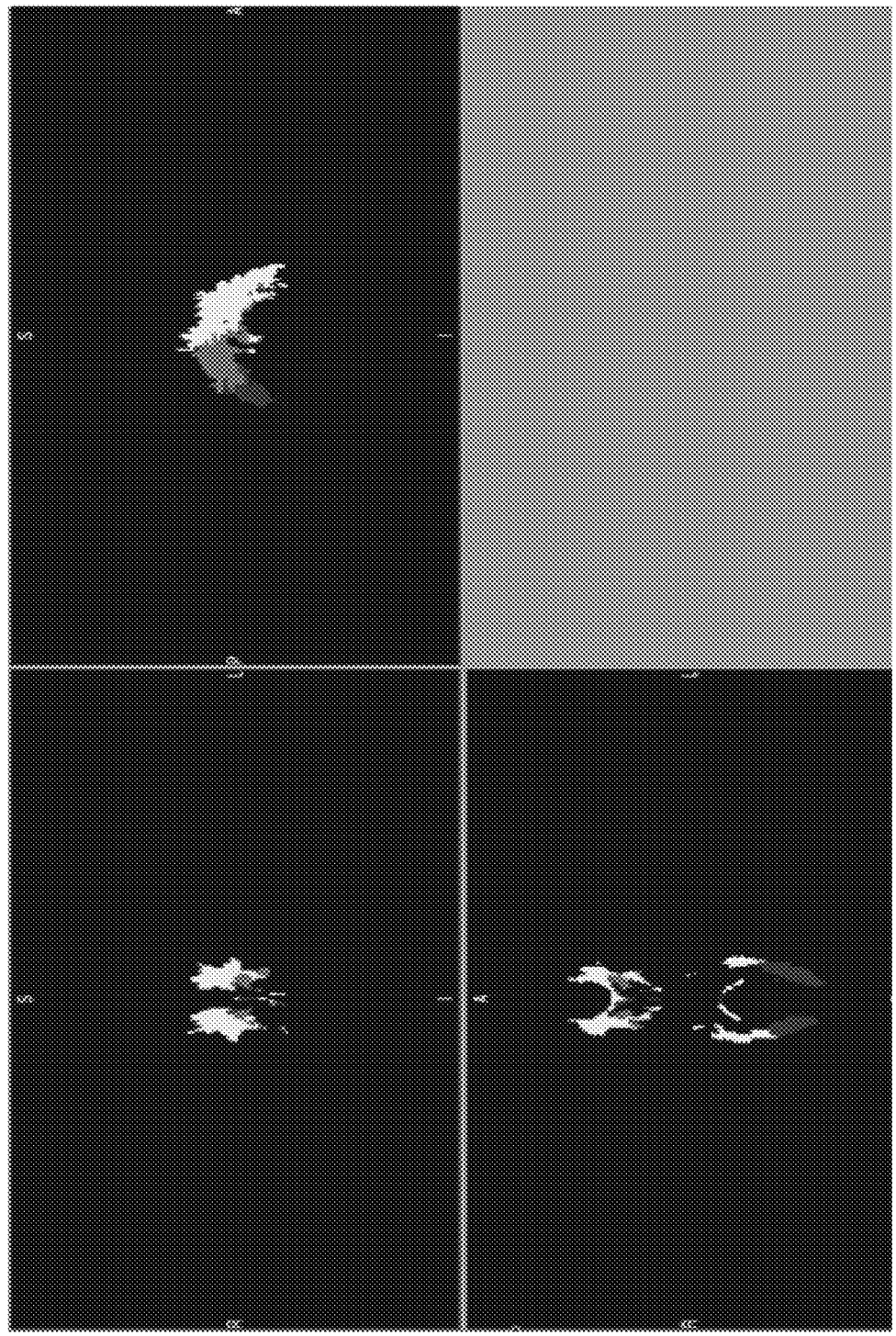
FIG. 4 shows a screenshot of an example embodiment of a regional WMH atlas according to the present disclosure.

FIG. 4 shows a screenshot of an example embodiment of a regional WMH atlas according to the present disclosure. As shown, the regional WMH atlas brain areas are visually distinct from each other, such as based on color, frequency, or shading, based on clustering frequency.

Figure 5:
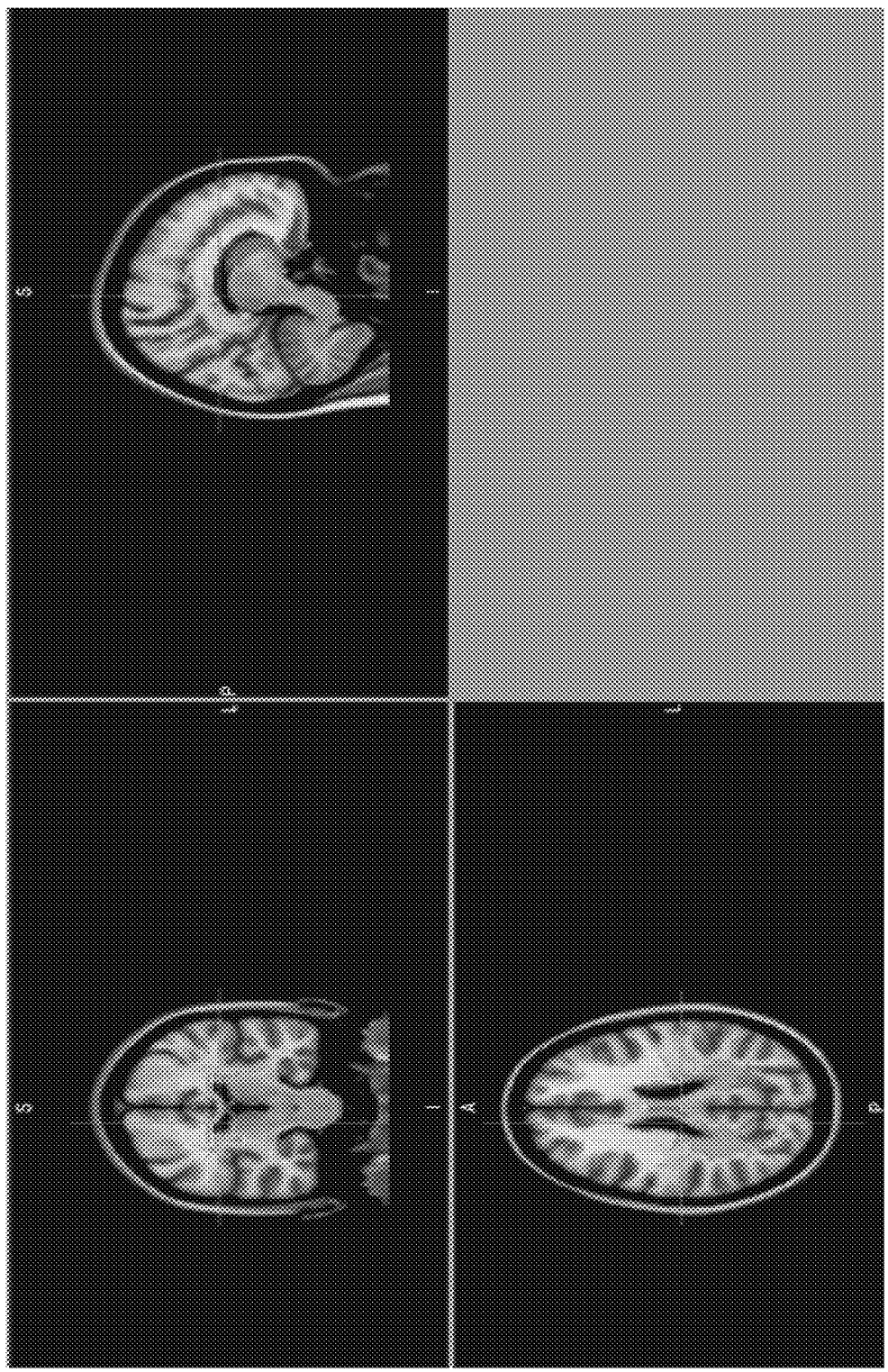
FIG. 5 shows a screenshot of an example embodiment of a regional WMH atlas overlaid onto a brain atlas according to the present disclosure.

FIG. 5 shows a screenshot of an example embodiment of a regional WMH atlas overlaid onto a brain atlas according to the present disclosure. As shown, the regional WMH atlas is overlaid onto the MNI atlas.

Figure 6:
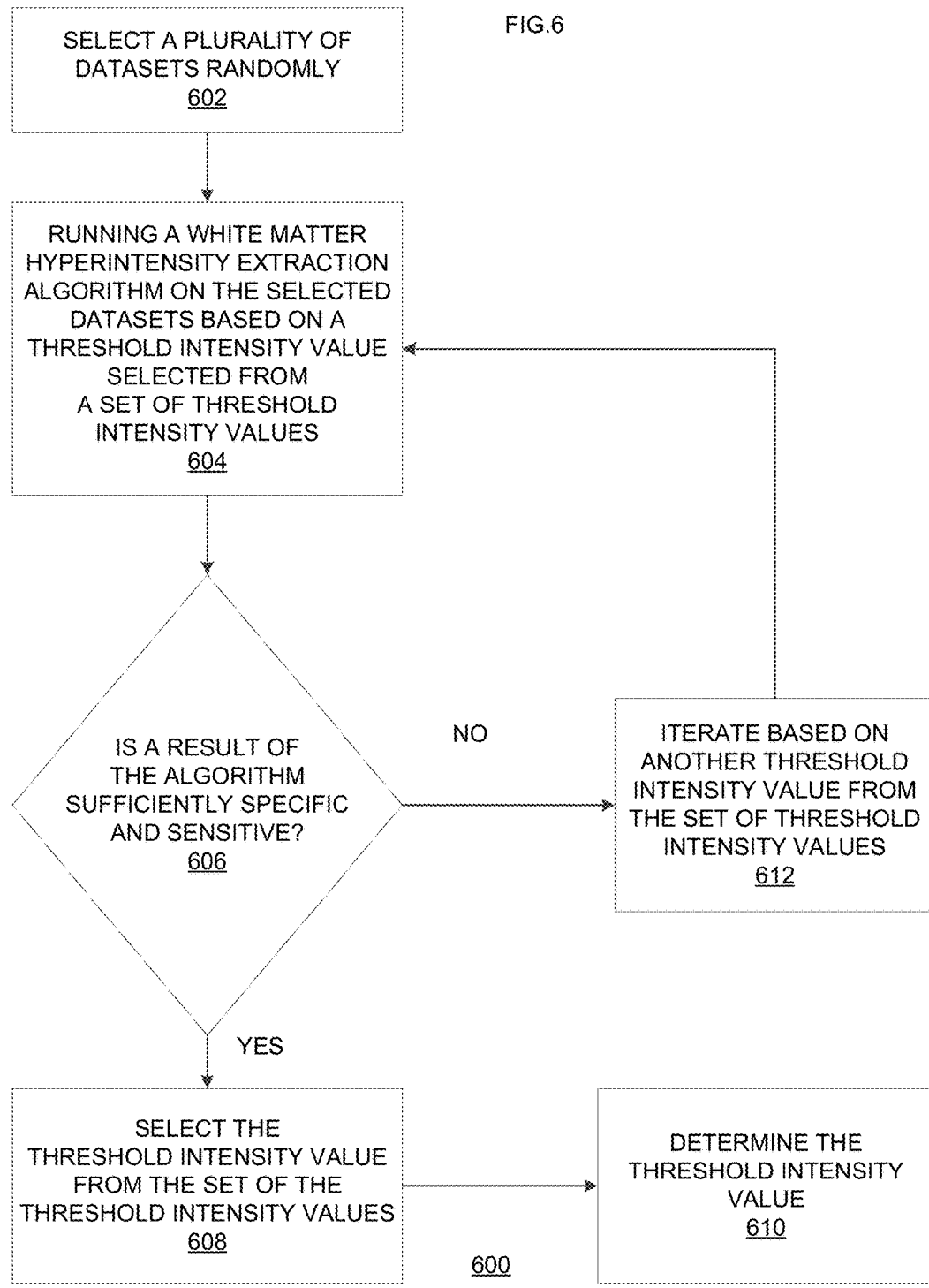
FIG. 6 shows a flowchart of an example embodiment of a process for determining a threshold intensity value according to the present disclosure.

FIG. 6 shows a flowchart of an example embodiment of a process for determining a threshold intensity value according to the present disclosure. A process 600 is used for threshold intensity value determination. The process 600 is performed via at least one actor, such as via a user operating the computer 100. The process 600 includes a plurality of blocks 602-612, which are performed consecutively. In some embodiments, the process 600 is performed within the process 200.

In block 602, the computer 100 selects a plurality of datasets randomly. The datasets comprise FLAIR imaging information. The datasets are selected from the datasets uniquely corresponding to the human subjects in the study, as described herein. For example, the computer 100 can be configured to select randomly between 5 to 10 datasets from the 253 datasets uniquely corresponding to the 253 human subjects, as described herein. However, note that the computer 100 can also be configured to select randomly less than 5 or more than 10 datasets from the datasets uniquely corresponding to the human subjects. The random selection is based on a random function executed via the computer 100.

In block 604, the computer 100 runs a WMH extraction algorithm on the selected datasets based on a threshold intensity value selected from a set of threshold intensity values. The computer 100 extracts WMH data from the FLAIR imaging information of the randomly selected datasets based on WMH being defined above the threshold value, such at least one standard deviation from a mean, for instance as being higher than 3 Sigma. The set of threshold intensity values is initially manually created, such as via a user. In other embodiments, the set of threshold intensity value is initially computer-generated based on computer vision/heuristics, as operated on a predetermined set of FLAIR imaging data.

In block 606, the computer 100 determines whether a result of the WMH extraction algorithm is sufficiently specific and sensitive. The process 600 continues to block 608 if the result of the WMH extraction algorithm is sufficiently specific and sensitive. The process 600 continues to block 612 if the result of the WMH extraction algorithm is not sufficiently specific and sensitive. The determination whether the result of the WMH extraction algorithm is sufficiently specific and sensitive can be based on receiving user input based on a user's impression of sensitivity/specificity optimization, as observed and input into the computer 100. Also, in order to reduce user involvement and increase automation, the computer 100 can choose a threshold value which gives the optimal specificity and sensitivity balance in a set of resulting WMH masks, as identified via the computer 100 via computer vision/heuristics based on a plurality of preset conditions, which can be updated dynamically, where at least one of the resulting WMH masks is nor over nor under labeled. For example, the computer 100 can be configured to account for a predetermined range of image specificity to image sensitivity threshold values and at least one of an image brightness information factor, a voxel location, a historical information of other images factor, an image degradation information factor, and an imaging machine information factor, such as based on a lookup table.

With respect to identification of WMH volumes, the computer 100 extracts the voxels from the subjects FLAIR scans, common to regional WMH atlas, and the computer 100 applies a curve fitting algorithm to the intensity values of these voxels. The computer 100 uses a normal distribution function as the curve is to be fitted. Based on a central limit theorem, which states that a sum of independent samples from any distribution with a finite mean and variance converges to the normal distribution as sample size goes to infinity, a normal or Gaussian distribution, also known as a bell curve is a defined by formula I above.

Accordingly, the Gaussian curve fitting provides a mean value and a standard deviation value. Such values are used as a reference to calculate the threshold intensity value, where the threshold Intensity is defined by mean+chosen Threshold Value*Standard Deviation (since WMH are higher than the mean intensity value). Therefore, all voxels with an intensity equal to or higher than the threshold intensity are labeled as WMH voxels. Subsequently, the computer 100 uses the regional WMH atlas to map out the regional distribution of such hyperintense voxels. The Gaussian curve fitting is shown in FIG. 9.

In block 608, the computer 100 selects the threshold intensity value from the set of threshold intensity values.

In block 610, the computer determines the threshold intensity value for subsequent use. For example, block 212 can now be performed.

In block 612, the computer 100 iterates based on another threshold intensity value from the set of threshold intensity values. The another value is different from the value of the threshold intensity value of block 604. Note that the computer 100 can display, such as via the display unit 110, a graphical user interface (GUI) containing a scale bar, a slider, a knob, a gradual level selector, a button, or other GUI element, which enables the user to adjust the threshold value for tailoring the user's analysis to a single subject. Accordingly, the user can manually select the another threshold intensity value. In other embodiments, the computer automatically selects the another threshold intensity value from the set of threshold intensity values, whether randomly or in an ordered manner.

Figure 7:
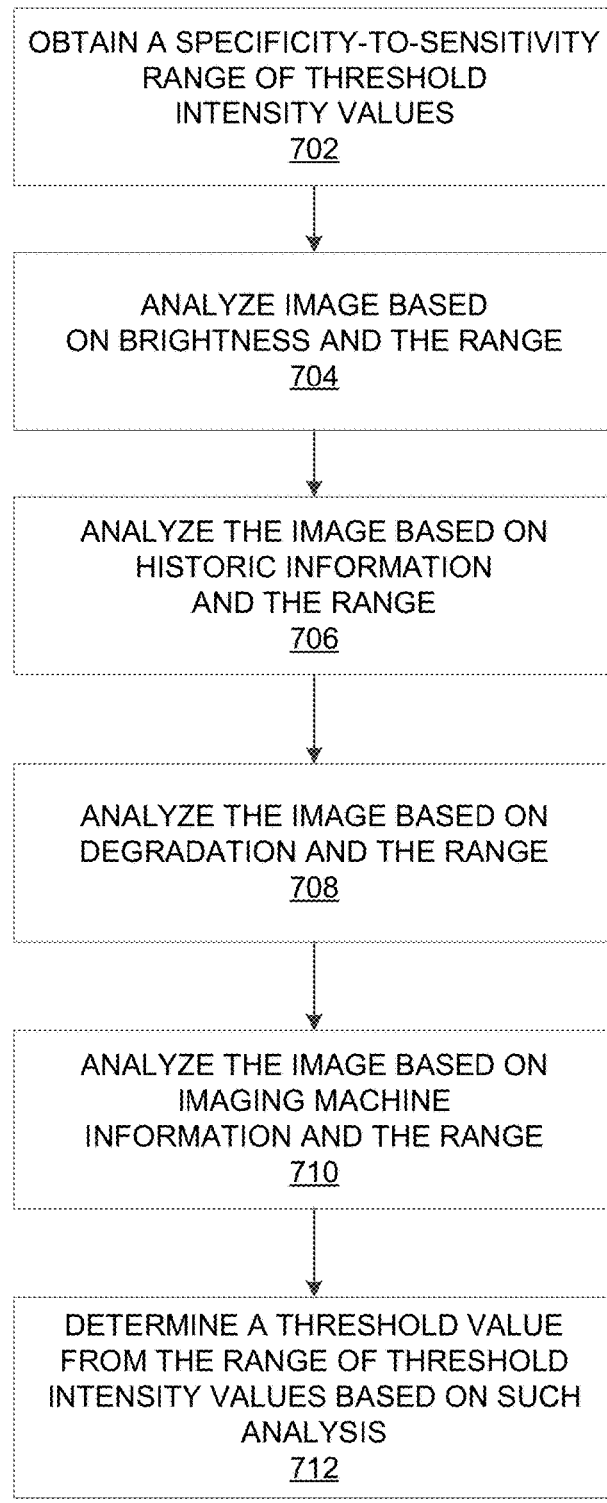
FIG. 7 shows a flowchart of an example embodiment of a process for image analysis according to the present disclosure.

FIG. 7 shows a flowchart of an example embodiment of a process for image analysis according to the present disclosure. A process 700 is used for image analysis to determine whether the result of the algorithm is sufficiently specific and sensitive, as described herein. The process 700 is performed via at least one actor, such as via a user operating the computer 100. The process 700 includes a plurality of blocks 702-714, which are performed consecutively. However, in other embodiments, non-consecutive performance is possible, such as blocks 704-712 being performed out of order in any way. Further, in some embodiments, the process 700 is performed within the process 200.

In block 702, the computer 100 obtains a specificity-to-sensitivity range of threshold intensity values. For example, a first end of the range provides that the threshold values in proximity of the first end enable high image specificity and a second end of the range provides that the threshold values in proximity of the second end enable high image sensitivity. The range can be manually generated. In other embodiments, the range is computer-generated.

In block 704, the computer 100 analyzes a WMH image based on image brightness information and the range, where the computer 100 is programmed to obtain a sufficiently visible, specific, yet sensitive image based on a set of user provided criteria.

In block 706, the computer 100 analyzes a WMH image based on image historic information and the range, where the computer 100 is programmed to obtain a sufficiently visible, specific, yet sensitive image based on a set of user provided criteria. The image historic information is based on appearance of other WMH images, as previously analyzed via the computer 100.

In block 708, the computer 100 analyzes a WMH image based on image degradation information and the range, where the computer 100 is programmed to obtain a sufficiently visible, specific, yet sensitive image based on a set of user provided criteria.

In block 710, the computer 100 analyzes a WMH image based on imaging machine information and the range, where the computer 100 is programmed to obtain a sufficiently visible, specific, yet sensitive image based on a set of user provided criteria. The imaging machine information enables analysis compensation based on quality of an imaging machine from which imaging data was obtained.

In block 712, the computer 100 determines a threshold value from the range of the threshold intensity values based on analysis from blocks 704-710.

Figure 8:
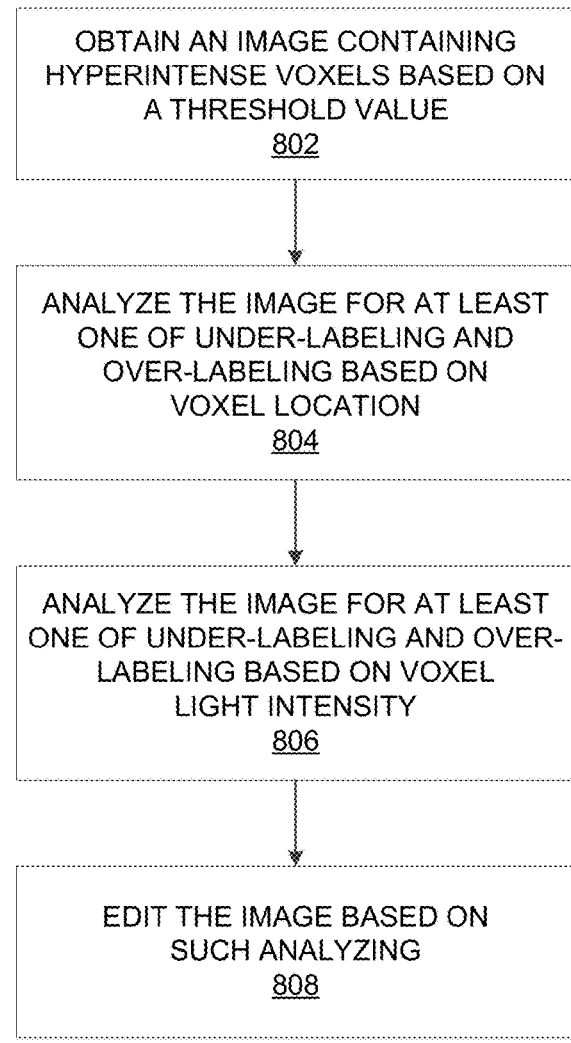
FIG. 8 shows a flowchart of an example embodiment of a process for quality analysis according to the present disclosure.

FIG. 8 shows a flowchart of an example embodiment of a process for quality analysis according to the present disclosure. A process 800 is used for image quality analysis.

The process 800 is performed via at least one actor, such as via a user operating the computer 100. The process 800 includes a plurality of blocks 802-808, which are performed consecutively. However, in other embodiments, non-consecutive performance is possible, such as blocks 804-806 being performed out of order in any way. Further, in some embodiments, the process 800 is performed within the process 200.

In block 802, the computer 100 obtains an image containing hyperintense voxels based on a threshold value.

In block 804, the computer 100 analyzes the image for at least one of under-labeling and over-labeling based on voxel location. For example, such analysis can be based on WMH historical data available to the computer 100.

In block 806, the computer 100 analyzes the image for at least one of under-labeling and over-labeling based on voxel light intensity. For example, such analysis can be based on WMH historical data available to the computer 100.

In block 808, the computer 100 edits the image based on blocks 804 and 806. For example, the computer 100 can label under-labeled image sections or un-label over-labeled image sections.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

In some embodiments, an apparatus or system comprise at least one processor, and memory storing instructions that, when executed by the at least one processor, cause the apparatus or system to perform one or more methodological acts as described herein. In some embodiments, the memory stores data, such as one or more structures, metadata, lines, tags, blocks, strings, or other suitable data organizations.

As will be appreciated by one skilled in the art, aspects of this disclosure can be embodied as a system, method or computer program product. Accordingly, aspects of the present disclosure can take the form of an entirely hardware embodiment, an entirely software embodiment (including firmware, resident software, micro-code, etc.) or as embodiments combining software and hardware aspects that can all generally be referred to herein as a "circuit," "module" or "system." Furthermore, aspects of the disclosure can take the form of a computer program product embodied in one or more computer readable medium(s) having computer readable program code embodied thereon.

Any combination of one or more computer readable medium(s) can be utilized. The computer readable medium can be a computer readable signal medium or a computer readable storage medium. A computer readable storage medium can be, for example, but not limited to, an electronic, magnetic, optical, electromagnetic, infrared, or semiconductor system, apparatus, or device, or any suitable combination of the foregoing. More specific example (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium can be any tangible medium that can contain, or store a program for use by or in connection with an instruction execution system, apparatus, or device.

A computer readable signal medium can include a propagated data signal with computer readable program code embodied therein, for example, in baseband or as part of a carrier wave. Such a propagated signal can take any of a variety of forms, including, but not limited to, electromagnetic, optical, or any suitable combination thereof. A computer readable signal medium can be any computer readable medium that is not a computer readable storage medium and that can communicate, propagate, or transport a program for use by or in connection with an instruction execution system, apparatus, or device.

Program code embodied on a computer readable medium can be transmitted using any appropriate medium, including but not limited to wireless, wireline, optical fiber cable, RF, etc., or any suitable combination of the foregoing.

Computer program code for carrying out operations for aspects of the present disclosure can be written in any combination of one or more programming language, including an object oriented programming language, such as Java, Smalltalk, C++ or the like and conventional procedural programming language, such as the "C" programming language or similar programming languages. The program code can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the steps can be performed in a differing order or steps can be added, deleted or modified. All of these variations are considered a part of the disclosure. It will be understood that those skilled in the art, both now and in the future, can make various improvements and enhancements which fall within the scope of the claims which follow.

The invention claimed is:

1. A method comprising:
   selecting, via a computer, an intensity threshold value;
   defining, via the computer, a plurality of hyperintensities on imaging data based on the intensity threshold value;
   extracting, via the computer, a plurality of voxels from the imaging data based on the defining;
   determining, via the computer, a total volume of the voxels based on the extracting; and
   determining, via the computer, a regional distribution of WMH based on an anatomical atlas and the total volume, wherein the intensity threshold value is selected from a range of specificity-to-sensitivity intensity threshold values.

2. The method of claim 1, wherein the selecting is based on an image analysis based on at least one of image brightness information, image historic information, image degradation information, or imaging machine information.

3. The method of claim 1, further comprising:
   analyzing, via the computer, the imaging data for at least one of hyperintensity under-labeling or hyperintensity over-labeling based on at least one of a voxel location or a voxel light intensity.

4. The method of claim 3, further comprising:
   editing, via the computer, the imaging data based on the analyzing.

5. A system comprising:
   a hardware processor;
   a memory operably coupled to the hardware processor, wherein the memory storing a set of instructions for execution via the hardware processor, wherein the set of instructions instructs the hardware processor to perform a method comprising:
   selecting an intensity threshold value;
   defining a plurality of hyperintensities on imaging data based on the intensity threshold value;
   extracting a plurality of voxels from the imaging data based on the defining;
   determining a total volume of the voxels based on the extracting; and
   determining a regional distribution of WMH based on an anatomical atlas and the total volume, wherein the intensity threshold value is selected from a range of specificity-to-sensitivity intensity threshold values.

6. The system of claim 5, wherein the selecting is based on image analysis based on at least one of image brightness information, image historic information, image degradation information, or imaging machine information.

7. The system of claim 5, wherein the method further comprising:
   analyzing the imaging data for at least one of hyperintensity under-labeling or hyperintensity over-labeling based on at least one of a voxel location or a voxel light intensity.

8. The system of claim 7, wherein the method further comprising:
   editing the imaging data based on the analyzing.

9. A non-transitory computer-readable storage medium storing a set of instructions for execution via a processing circuit to implement a method comprising:
   selecting, via a computer, an intensity threshold value;
   defining, via the computer, a plurality of hyperintensities on imaging data based on the intensity threshold value;
   extracting, via the computer, a plurality of voxels from the imaging data based on the defining;
   determining, via the computer, a total volume of the voxels based on the extracting; and
   determining, via the computer, a regional distribution of WMH based on an anatomical atlas and the total volume, wherein the intensity threshold value is selected from a range of specificity-to-sensitivity intensity threshold values.

10. The non-transitory computer-readable storage medium of claim 9, wherein the selecting is based on image analysis based on at least one of image brightness information, image historic information, image degradation information, or imaging machine information.

11. The non-transitory computer-readable storage medium of claim 9, wherein the method further comprising:
analyzing, via the computer, the imaging data for at least one of hyperintensity under-labeling or hyperintensity over-labeling based on at least one of a voxel location or a voxel light intensity.

12. The non-transitory computer-readable storage medium of claim 11, wherein the method further comprising:
editing, via the computer, the imaging data based on the analyzing.

13. A method comprising:
selecting, via a computer, an intensity threshold value;
defining, via the computer, a plurality of hyperintensities on imaging data based on the intensity threshold value;
analyzing, via the computer, the imaging data for at least one of hyperintensity under-labeling or hyperintensity over-labeling based on at least one of a voxel location or a voxel light intensity;
extracting, via the computer, a plurality of voxels from the imaging data based on the defining;
determining, via the computer, a total volume of the voxels based on the extracting; and
determining, via the computer, a regional distribution of WMH based on an anatomical atlas and the total volume.

14. The method of claim 13, wherein the intensity threshold value is selected from a range of specificity-to-sensitivity intensity threshold values.

15. The method of claim 13, wherein the selecting is based on an image analysis based on at least one of image brightness information, image historic information, image degradation information, or imaging machine information.

16. The method of claim 13, further comprising:
editing, via the computer, the imaging data based on the analyzing.

17. A system comprising:
a hardware processor;
a memory operably coupled to the hardware processor, wherein the memory storing a set of instructions for execution via the hardware processor, wherein the set of instructions instructs the hardware processor to perform a method comprising:
selecting an intensity threshold value;
defining a plurality of hyperintensities on imaging data based on the intensity threshold value;
analyzing the imaging data for at least one of hyperintensity under-labeling or hyperintensity over-labeling based on at least one of a voxel location or a voxel light intensity;
extracting a plurality of voxels from the imaging data based on the defining;
determining a total volume of the voxels based on the extracting; and
determining a regional distribution of WMH based on an anatomical atlas and the total volume.

18. The system of claim 17, wherein the intensity threshold value is selected from a range of specificity-to-sensitivity intensity threshold values.

19. The system of claim 17, wherein the selecting is based on image analysis based on at least one of image brightness information, image historic information, image degradation information, or imaging machine information.

20. The system of claim 17, wherein the method further comprising:
editing the imaging data based on the analyzing.

21. A non-transitory computer-readable storage medium storing a set of instructions for execution via a processing circuit to implement a method comprising:
selecting, via a computer, an intensity threshold value;
defining, via the computer, a plurality of hyperintensities on imaging data based on the intensity threshold value;
analyzing, via the computer, the imaging data for at least one of hyperintensity under-labeling or hyperintensity over-labeling based on at least one of a voxel location or a voxel light intensity;
extracting, via the computer, a plurality of voxels from the imaging data based on the defining;
determining, via the computer, a total volume of the voxels based on the extracting; and
determining, via the computer, a regional distribution of WMH based on an anatomical atlas and the total volume.

22. The non-transitory computer-readable storage medium of claim 21, wherein the intensity threshold value is selected from a range of specificity-to-sensitivity intensity threshold values.

23. The non-transitory computer-readable storage medium of claim 21, wherein the selecting is based on image analysis based on at least one of image brightness information, image historic information, image degradation information, or imaging machine information.

24. The non-transitory computer-readable storage medium of claim 21, wherein the method further comprising:
editing, via the computer, the imaging data based on the analyzing.

* * * * *